United States Patent
Zentz et al.

(10) Patent No.: US 6,196,840 B1
(45) Date of Patent: Mar. 6, 2001

(54) CUSTOM FITTING VARIABLE DIMENSION DENTAL IMPRESSION TRAY, PRODUCT AND METHOD

(75) Inventors: Ronald R. Zentz; Andrew M. Lichkus, both of York; Fredric J. Weber, Thomasville, all of PA (US)

(73) Assignee: Dentsply Research & Development Corp., Los Angeles, CA (US)

( * ) Notice: Subject to any disclaimer, the term of this patent is extended or adjusted under 35 U.S.C. 154(b) by 0 days.

(21) Appl. No.: 09/356,277

(22) Filed: Jul. 16, 1999

Related U.S. Application Data
(60) Provisional application No. 60/096,579, filed on Aug. 14, 1998.

(51) Int. Cl.$^7$ .................................................. A61C 9/00
(52) U.S. Cl. ........................ 433/71; 433/48; 433/214
(58) Field of Search .................. 433/37, 48, 214, 433/71

(56) References Cited

U.S. PATENT DOCUMENTS

| | | |
|---|---|---|
| 637,123 | 11/1899 | Jackson . |
| 1,083,156 | 12/1913 | Telle . |
| 1,955,709 | 4/1934 | Kinsley ........................ 32/6 |
| 2,466,727 | 4/1949 | Morgan ........................ 32/2 |
| 2,588,169 | 3/1952 | Shea ........................... 32/19 |
| 2,634,500 * | 4/1953 | McAdoo ................. 433/48 X |
| 2,674,798 | 4/1954 | Craigo ........................ 32/19 |
| 2,790,237 | 4/1957 | Chaiken ...................... 32/2 |

(List continued on next page.)

FOREIGN PATENT DOCUMENTS

| | | |
|---|---|---|
| 32 39 529 | 5/1984 | (DE) . |
| 4103991 * | 9/1992 | (DE) ............................. 433/48 |
| 074 182 | 3/1983 | (EP) . |
| 443 270 | 8/1991 | (EP) . |
| 443269 | 8/1991 | (EP) . |
| 566 221 | 10/1993 | (EP) . |
| 90/14052 | 11/1990 | (WO) . |
| 91/127777 | 9/1991 | (WO) . |
| 95/35071 | 12/1995 | (WO) . |
| 96/32901 | 10/1996 | (WO) . |
| 97/43979 | 11/1997 | (WO) . |

OTHER PUBLICATIONS

Journal of Prosthetic Dentistry, Dec. 1991, vol. 66, #6 pp. 821–822.

CAPA®650, Solvay Caprolactones; Issue I/Mar. 1998; p. 1 of 1.

CAPA®600 Series, Solvay Caprolactones, Issue I/Mar. 1998, p. 3 of 3.

*Primary Examiner*—Nicholas D. Lucchesi
(74) *Attorney, Agent, or Firm*—Dale R. Lovercheck; James B. Bieber

(57) ABSTRACT

The invention provides a heat formable tray having a bite block and a method of forming the tray to a patient and forming a final impression in a single visit to the dental office by the patient. A custom fitting variable dimension bite registration dental impression tray, is provided which includes a bite registration member, and a dental impression tray. The dental impression tray comprises a heat adjustable material having a softening point above 38 ° C. and below 120 ° C. The variable dimension bite registration dental impression tray is used in a method for making an impression of dental tissue, comprising the steps of: a) providing a variable dimension bite registration dental impression tray, b) heating the dental impression tray to softened state, c) adjusting the dimensions of the dental impression tray, d) cooling the heat adjustable material so that it solidifies; and e) enveloping the tissue with the dental impression material, whereby a final dental tissue impression is obtained.

29 Claims, 7 Drawing Sheets

U.S. PATENT DOCUMENTS

| | | | |
|---|---|---|---|
| 2,802,269 | 8/1957 | Stern | 32/17 |
| 2,963,786 | 12/1960 | Browning | 32/17 |
| 3,056,205 | 10/1962 | Ennor | 32/19 |
| 3,241,238 | 3/1966 | Kersten | 32/2 |
| 3,293,748 | 12/1966 | Skinner | 32/19 |
| 3,464,111 | 9/1969 | Gillard | 32/2 |
| 3,465,440 | 9/1969 | Gareis | 32/2 |
| 3,473,225 | 10/1969 | Deuschle et al. | 32/17 |
| 4,019,253 | 4/1977 | Hazar | 32/19 |
| 4,097,992 | 7/1978 | Hazar | 32/2 |
| 4,145,812 | 3/1979 | Johnson et al. | 32/17 |
| 4,227,877 | 10/1980 | Tureaud et al. | 433/37 |
| 4,235,594 | 11/1980 | Schwartz | 433/68 |
| 4,245,988 | 1/1981 | Cinotti et al. | 433/68 |
| 4,247,287 | 1/1981 | Gigante | 433/199 |
| 4,259,074 | 3/1981 | Link | 433/214 |
| 4,361,528 | 11/1982 | Ginsburg et al. | 264/28 |
| 4,375,965 | 3/1983 | Weissman | 433/37 |
| 4,401,616 | 8/1983 | Wagner | 264/138 |
| 4,413,979 | 11/1983 | Ginsburg et al. | 433/41 |
| 4,457,713 | 7/1984 | Schneider | 433/171 |
| 4,569,342 | 2/1986 | Von Nostitz | 128/136 |
| 4,657,509 | 4/1987 | Morris | 433/37 |
| 4,768,951 | 9/1988 | Abiru, et al. | 433/48 |
| 4,881,713 | 11/1989 | Wise | 249/54 |
| 5,011,407 | 4/1991 | Pelerin | 433/48 |
| 5,066,231 | 11/1991 | Oxman et al. | 433/214 |
| 5,112,225 | 5/1992 | Diesso | 433/48 |
| 5,135,392 | 8/1992 | Polansky | 433/37 |
| 5,266,031 | 11/1993 | Marigza | 433/71 |
| 5,267,862 | 12/1993 | Parket | 433/215 |
| 5,336,086 | 8/1994 | Simmen et al. | 433/37 |
| 5,414,544 | 6/1995 | Oxman et al. | 433/48 |
| 5,431,563 * | 7/1995 | Huybrechts | 433/48 |
| 5,503,552 * | 4/1996 | Diesso | 433/48 X |
| 5,562,449 * | 10/1996 | Jacobs et al. | 433/215 |
| 5,591,786 * | 1/1997 | Oxman et al. | 523/109 |
| 5,753,781 * | 5/1998 | Oxman et al. | 525/415 |
| 5,794,627 * | 8/1998 | Frantz et al. | 128/848 |
| 5,961,325 * | 10/1999 | Van Handel | 433/37 |

* cited by examiner

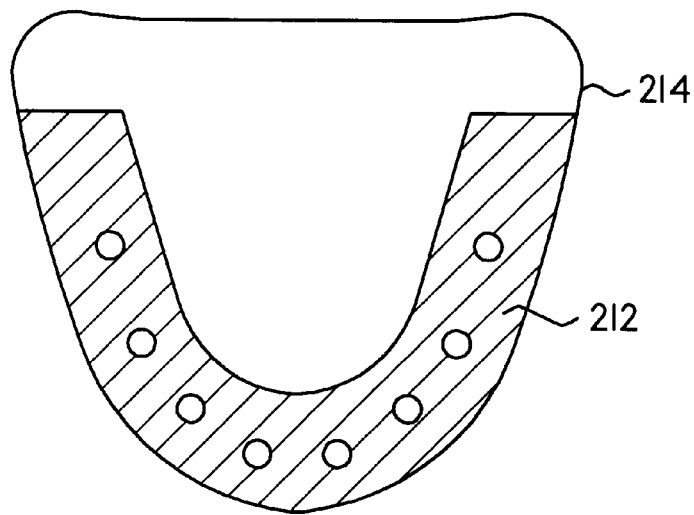
_Fig_-12
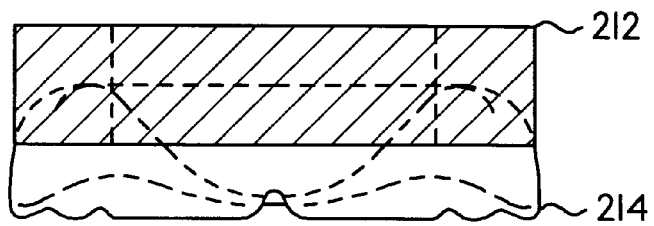
_Fig_-13
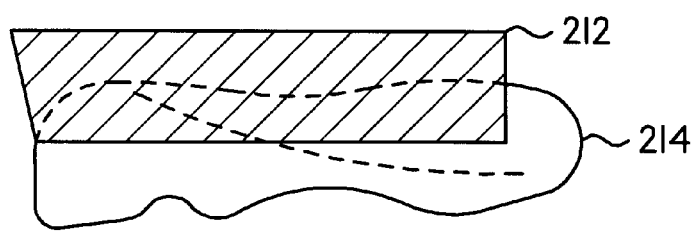
_Fig_-14

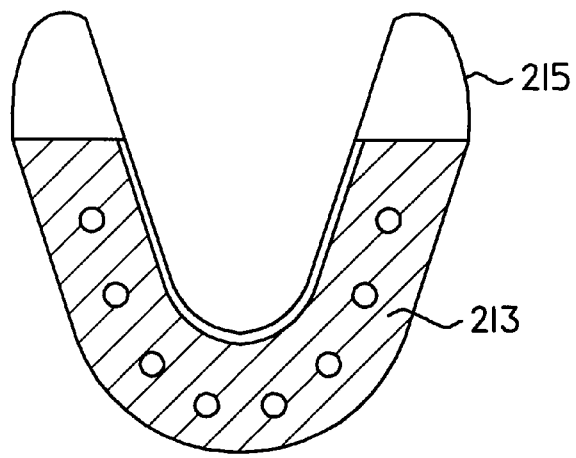
_Fig_-15
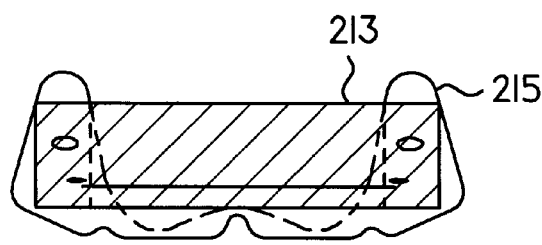
_Fig_-16
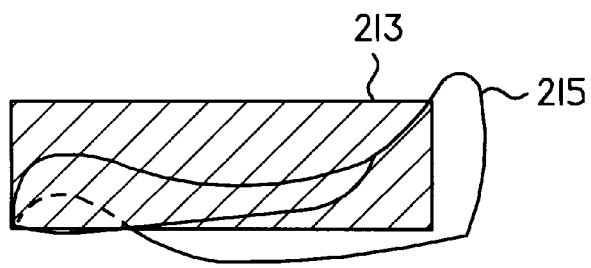
_Fig_-17

CUSTOM FITTING VARIABLE DIMENSION DENTAL IMPRESSION TRAY, PRODUCT AND METHOD

This is a continuation-in-part of provisional patent application Ser. No. 06/096,579 filed Aug. 14, 1998. The invention relates to dental bite block impression trays. More specifically the invention provides a custom-fitting bite block impression tray, having a tray which is adjustable while heated. The method of the invention provides a final dental impression, bite registration and tooth position record during a single visit to a dental office by a patient for the manufacture of removable dentures.

BACKGROUND OF THE INVENTION

Traditional impressioning systems employ one or more low viscosity, flowable elastomeric materials such as an alginate, hydrocolloid, polyvinylsiloxane, polyether, or polysulfide contained in a fairly rigid adhesive-coated plastic or metal arch-shaped tray. The elastomeric material often is applied both to the dental tissue to be modeled and to the tray. The elastomeric material and surrounding tray are subsequently pressed against the dental tissue, and left in place until the elastomeric material has hardened.

Diesso in U.S. Pat. No. 5,112,225 discloses dental trays made of at least 75% by weight polycaprolactone.

Krantz, et al disclose an impression in a tray with a wax rim as seen in FIG. 1, in the Journal of Prosthetic Dentistry, December 1991, Vol. 66, #6 pages 821–822. Making final impressions of a patient's mouth requires a first step of a preliminary impression which records the general shape of the patient's gums. In the second step, a final impression with a custom tray forms a more detailed impression of the patient's gums. Vertical dimension and tooth position are recorded by adjustment of a wax rim followed by articulation of the upper and lower jaws to each other (bite registration). The two impression steps require separate visits to the dental office by the patient. Following this, dental casts are poured, baseplates are fabricated and the artificial teeth are positioned in wax for use in making a denture for the patient.

Oxman et al in U.S. Pat. No. 5,591,786 disclose semi-thermoplastic molding compositions which include polycaprolactones. Diesso in U.S. Pat. No. 5,112,225 discloses a custom dental tray formed from polycaprolactones. High molecular weight poly (epsilon-caprolactone) (also known as "polycaprolactone") has been used as a thermoplastic molding compound for dentistry.

The prior art does not disclose a custom fitting variable dimension bite registration dental impression tray, comprising: a bite registration member, and a heat adjustable variable dimension dental impression tray.

The problems of the prior art are overcome by the present invention. The invention provides a custom fitting tray which is adaptable to the dimensions of a patient's dental tissue and useful for forming a final impression and capturing an occlusal record (bite registration) during a single visit to the dental office by the patient. Additionally, the wax rims are contoured and shaped to mimic the final position of the denture teeth.

"Esthetic record" as used herein refers to a bite registration member (preferably a wax rim) modified to a final position and marked to record information about the position of prosthetic teeth.

"Occlusal record" as used herein refers by a bilateral holding member (made of occlusal record material), which affixes upper and lower bite registration members (preferably a wax rims) in a position representative of the patient's jaw relationship.

Bite registration members are preferably made of wax.

OBJECTS OF THE INVENTION

It is an object of the invention to provide a final impression of a patient's mouth and the patient's bite registration in a wax rim.

It is an object of the invention to provide a custom fitting variable dimension bite registration dental impression tray, comprising: a bite registration member (wax rim), and a heat adjustable variable dimension dental impression tray.

It is an object of the invention to provide a custom fitting variable dimension bite registration dental impression tray comprising a variable dimension support composed of polycaprolactone.

It is an object of the invention to provide a custom fitting variable dimension bite registration dental impression tray having a wax bite registration and "esthetic record" member.

It is an object of the invention to provide a custom fitting variable dimension bite registration dental impression tray, comprising a bite registration member, and a dental impression tray, the bite registration member comprising readily shaveable and inscribable material, the dental impression tray comprising a heat adjustable material having a softening point above 38° C. and below 120° C.

A final dental tissue impression as used herein refers to a dental tissue impression from which a final cast of a patient's dental tissue is made to form a dental prosthesis, such as a denture, that fits closely to the patient's dental tissue.

Custom fitting as used herein refers to the ability to be shaped and/or shaping to fit a variable dimension bite registration dental impression tray to a particular patient's dental tissue.

Softening point of a material as used herein refers to a temperature just sufficient for the material to moldably deform under pressures of from 800 psi to 10 psi.

Heat formable material as used herein refers to a material having a softening point above 38° C. and below 120° C.

BRIEF DESCRIPTION OF THE DRAWING

FIG. 12 is a top view of the top custom fitting variable dimension bite registration dental impression tray shown in FIGS. 4 and 5, with the bite registration member.

FIG. 13 is a front view of the top custom fitting variable dimension bite registration dental impression tray shown in FIGS. 4 and 5, with the bite registration member.

FIG. 14 is a side view of the top custom fitting variable dimension bite registration dental impression tray shown in FIGS. 4 and 5, with the bite registration member.

FIG. 15 is a top view of the bottom custom fitting variable dimension bite registration dental impression tray shown in FIGS. 4 and 5, with the bite registration member.

FIG. 16 is a front view of the bottom custom fitting variable dimension bite registration dental impression tray shown in FIGS. 4 and 5, with the bite registration member.

FIG. 17 is a side view of the bottom custom fitting variable dimension bite registration dental impression tray shown in FIGS. 4 and 5, with the bite registration member.

SUMMARY OF THE INVENTION

The invention provides a dental wax bite block impression tray and method of forming a variable dimension tray to a patient and forming a final impression in a single visit to the dental office by the patient. A custom fitting variable dimension bite registration dental impression tray, is provided which includes a bite registration member, and a dental impression tray, The dental impression tray comprises a heat adjustable material having a softening point above 38° C. and below 120° C. The variable dimension bite registration dental impression tray is used in a method for making an impression of dental tissue, comprising the steps of: a) providing a variable dimension bite registration dental impression tray, comprising a bite registration member, and a dental impression tray, the dental impression tray supporting dental impression material, b) heating the dental impression tray to softened state, the heat adjustable material being solid at 38° C. and having a softening point that comfortably can be withstood by oral tissues, c) adjusting the dimensions of the dental impression tray, d) cooling the heat adjustable material so that it solidifies; and e) enveloping the tissue with the dental impression material carried by the tray, whereby a dental tissue impression is obtained.

DETAILED DESCRIPTION OF THE INVENTION

Figure 1:
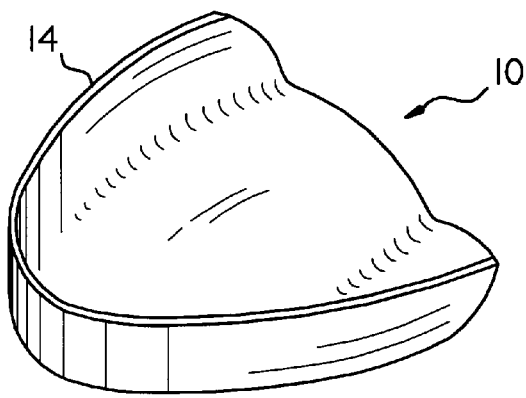
FIG. 1 is a perspective view of a custom fitting variable dimension dental impression tray, (providing heat adjustable variable dimension support for impression material) in accordance with the invention.
Figure 1A:
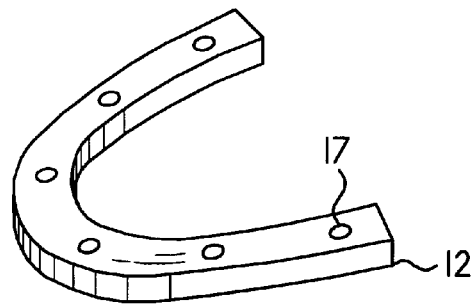
FIG. 1A is a perspective view of a bite registration member for use with a dental impression trays in accordance with the invention.
Figure 1B:
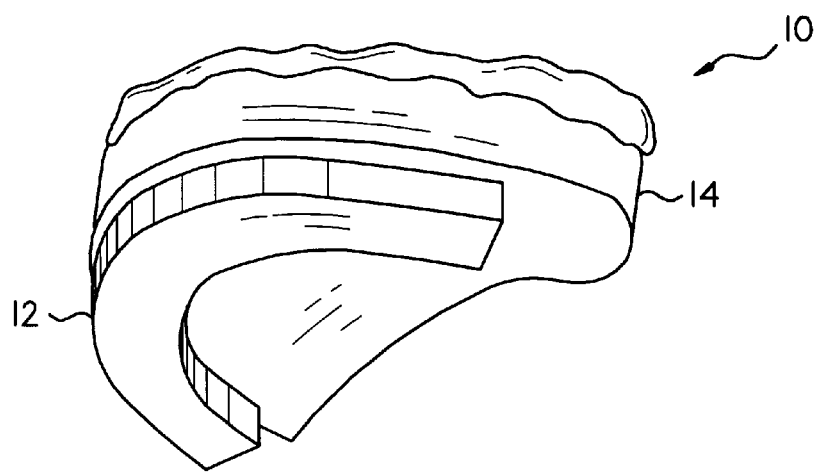
FIG. 1B is a perspective view of a custom fitting variable dimension bite registration dental impression trays in accordance with the invention.

The invention is now described with more particular reference to FIGS. 1 through 17. With more particular reference to FIG. 1 is seen custom fitting variable dimension dental impression tray 10. Variable dimension bite registration dental impression tray 10 comprises a bite registration member 12, U-shaped a dental impression tray 14 formed from a heat adjustable variable dimension support. With more particular reference to FIG. 1A is seen U-shaped bite registration member 12 having protrusions 17 for use in affixing bite registration member 12 to dental impression tray 14. Protrusions 17 extend outwardly from the upper surface of bite registration member 12 and are distributed along bite registration member 12 in a U-shape. FIG. 1B shows upper custom fitting variable dimension dental impression tray 10 affixed to a lower tray and each tray supporting a final dental impression and each tray having a bite registration member. Variable dimension dental impression tray 10 comprises a bite registration member 12, U-shaped a dental impression tray 14 formed from a heat adjustable variable dimension support.

Figure 2:
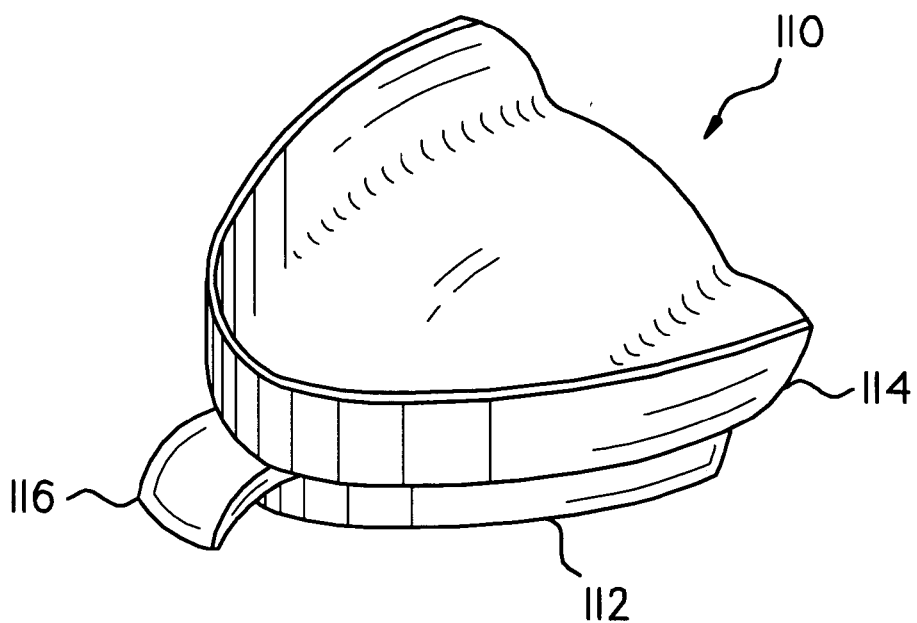
FIG. 2 is a perspective view of a custom fitting variable dimension bite registration dental impression tray, comprising a bite registration member and a dental impression tray (providing heat adjustable variable dimension support for impression material) in accordance with the invention.
Figure 3:
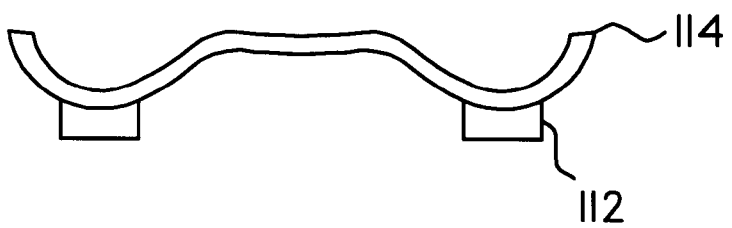
FIG. 3 is a cross-sectional end view of the tray shown in FIG. 2.

With more particular reference to FIGS. 2 and 3 is seen custom fitting variable dimension bite registration dental impression tray 110. U-shaped variable dimension bite registration dental impression tray 110 comprises a U-shaped bite registration member 112, a dental impression tray 114 formed from a heat adjustable variable dimension support. Tab 116 is connected to tray 114.

Figure 4:
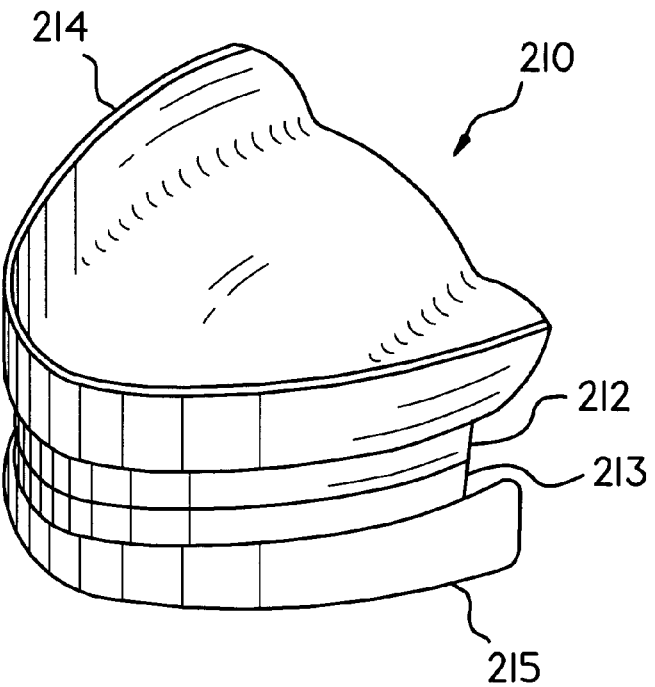
FIG. 4 is a perspective view of a pair of custom fitting variable dimension bite registration dental impression trays, fixed in centric relation in accordance with the invention.
Figure 5:
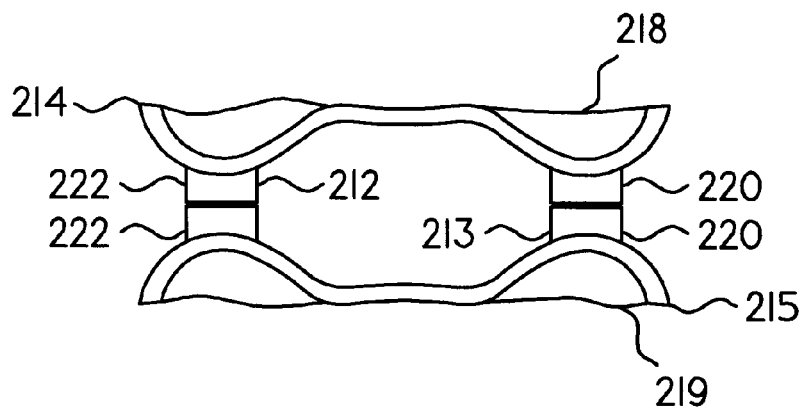
FIG. 5 is a cross-sectional end view of the pair of trays shown in FIG. 4.
Figure 6:
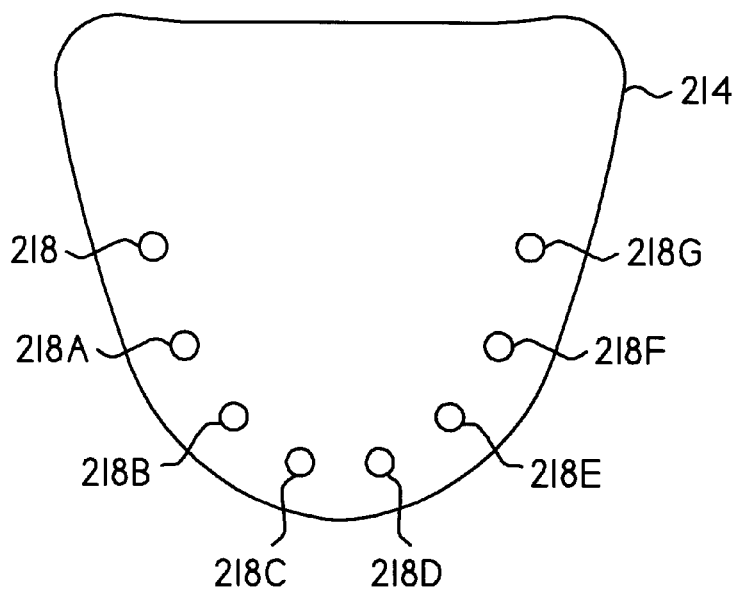
FIG. 6 is a top view of the top custom fitting variable dimension bite registration dental impression tray shown in FIGS. 4 and 5, except without the bite registration member.
Figure 7:
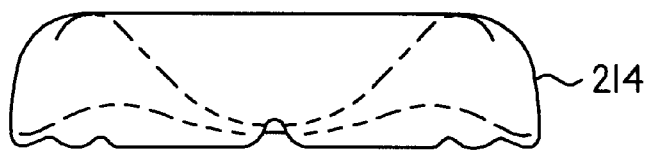
FIG. 7 is a front view of the top custom fitting variable dimension bite registration dental impression tray shown in FIGS. 4 and 5, except without the bite registration member.
Figure 8:
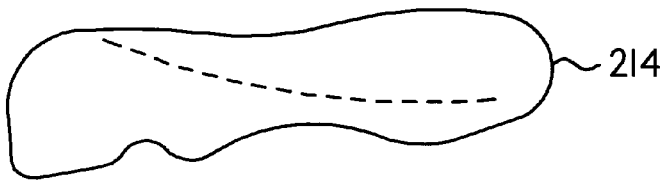
FIG. 8 is a side view of the top custom fitting variable dimension bite registration dental impression tray shown in FIGS. 4 and 5, except without the bite registration member.
Figure 9:
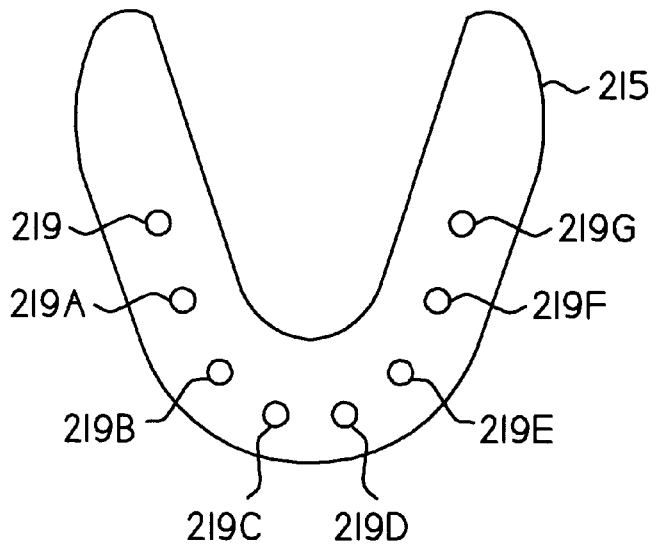
FIG. 9 is a top view of the bottom custom fitting variable dimension bite registration dental impression tray shown in FIGS. 4 and 5, except without the bite registration member.
Figure 10:
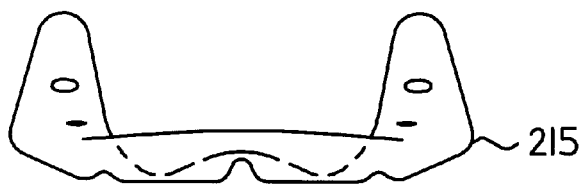
FIG. 10 is a front view of the bottom custom fitting variable dimension bite registration dental impression tray shown in FIGS. 4 and 5, except without the bite registration member.
Figure 11:
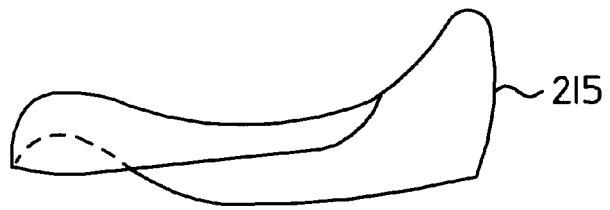
FIG. 11 is a side view of the bottom custom fitting variable dimension bite registration dental impression tray shown in FIGS. 4 and 5, except without the bite registration member.

With more particular reference to FIGS. 4 through 17 is seen upper and lower variable dimension bite registration dental impression trays 214 and 215. As shown in FIGS. 4 and 5 trays 214 and 215 are held as a pair by occlusal record material in a position representative of the patient's centric occlusal (jaw) relationship. The pair of U-shaped trays 210 includes upper U-shaped tray 214 and lower tray 215. Upper tray 214 is adhered to wax bite registration member 212 and has circular recesses 218 through 218G distributed along the bottom surface in a U-shape. Each tray is U-shaped in cross section. Recesses 218 through 218G may extend through upper tray 214 to form aperatures. Lower tray 215 has wax bite registration member 213 and circular recesses 219 through 219G distributed along the upper surface in a U-shape. Recesses 219 through 219G may extend through lower tray 215 to form aperatures. Wax bite registration member 212 is warmed to its melting point and applied to upper tray 214. Prior to cooling a portion of the wax from wax bite registration member 212 flows into circular recesses 218 through 218G. Upon cooling the wax in recesses 218 through 218G hold wax bite registration member 212 to upper tray 214. Similarly, wax bite registration member 213 is warmed to its melting point and applied to lower tray 215. Prior to cooling a portion of the wax from wax bite registration member 213 flows into circular recesses 219. Upon cooling the wax in recesses 219 through 219G hold wax bite registration member 213 to lower tray 215. Bite registration members 212 and 213 are affixed by occlusal record material 220 and 222 in a position representative of the patient's centric occlusal (jaw) relationship after trays are adapted and impressions have been made of oral tissues.

Heat adjustable variable dimension support is made of a composition that is heat adjustable to change the dimensions of the support. The desired properties of the heat adjustable composition is that it has molten or softened ("warm") and solid ("cool") states. The warm state is characterized by appreciable mass flow of the molding composition under moderate (hand) pressure at some temperature between body temperature (about 38° C.) and the maximum temperature that comfortably can be withstood by oral tissues. This maximum temperature is generally thought to be about 75°

C. (167° F.), although a maximum of about 65° C. (149° F.). is preferred. The cool state is characterized by sufficient strength and stiffness to serve as a custom dental impression tray at or below body temperature (38° C.). The warm and cool state properties permit the molding composition to be heated to a moderate temperature, manually shaped in the mouth while warm to conform to the shape of hard and soft oral tissue, and cooled within the mouth to form a substantially rigid tray. Various dental impression materials may then be used in the rigid tray to make an acceptably accurate dental impression.

Representative heat adjustable compositions include polyesters and polyurethanes such as those described in U.S. Pat. Nos. 3,382,202, 4,059,715, 4,182,829, 4,327,013, 4,361,538, 4,552,906 and 4,569,342, and copolymers such as those described in U.S. Pat. Nos. 4,659,786, 4,740,245 and 4,768,951. The thermoplastic material preferably is a homopolymer or copolymer of epsilon-caprolactone. The polycaprolactone optionally can contain property-modifying or cross-linkable functional groups (for example hydroxyl, acrylate, methacrylate, epoxy, isocyanato or vinyl groups) if desired.

Preferred polycaprolactones have the formula:

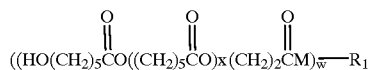

where $R_1$ is an aromatic or a straight chain or branched aliphatic backbone, which can optionally contain one or more non-interfering substituents such as hydroxyl or amine groups, w is 1 if $R_1$ is hydrogen, and w otherwise has an average value of about 1 to about 4, M is oxygen or —$NR_2$— where $R_2$ is hydrogen or a non-interfering aromatic or aliphatic group, and the product of w times x is greater than about 35.

Blends of polycaprolactones can also be employed as heat adjustable compositions. Commercially available polycaprolactone polymers include "TONE P-700" and "TONE P-767" (40,000 molecular weight) and "TONE P-300" (10,000 molecular weight) polycaprolactone from Union Carbide Corp., and the "CAPA" polycaprolactones "630" (30,000 molecular weight), "640" (40,000 molecular weight), "650" (50,000 molecular weight), and "656" (56,000 molecular weight) from Interox.

Polycaprolactone powder is preferably mixed with an amorphus polymer powder, such as ABS polymer powder, in a weight ratio of from about 0.1 parts to about 10 parts of polycaprolactone powder to about 1 part of amorphus polymer powder to form a molding composition useful for making trays in accordance with the invention.

The molding compositions used in the invention can contain a wide variety of adjuvants depending upon the desired end use. Suitable adjuvants include solvents, diluents, plasticizers, pigments, dyes, inorganic or organic fibrous or particulate reinforcing or extending fillers, thixotropic agents, indicators, inhibitors, stabilizers, UV absorbers, medicaments (e.g., leachable fluorides), biocides and the like. For custom tray applications, the molding composition preferably contains one or more fillers. The types and amounts of ingredients in the molding compositions of the invention usually will be empirically selected.

Transforming the molding composition from a warm state to a cool state requires loss of thermal energy and can be carried out using a variety of cooling techniques. Cooling can take place under ambient conditions in the presence of air only. Cooling can be expedited using forced air, cold water, ice, or heat sinks such as chilled "cold packs" or flexible pouches containing low boiling inert liquids.

A custom impression tray is formed from a moldable composition and filled with a conventional elastomeric impression material (for example, a silicone elastomer). By shaping the tray in the mouth before it is filled with elastomer, the tray volume and required amount of elastomer will be minimized. Custom impression trays can be used to prepare crowns, bridges, dentures, splints and pontics. The material can also be used to prepare shapeable orthopedic casts and splints.

In accordance with a preferred embodiment of the invention, trays are formed of a polymeric material having improved tensile strength, flexural modulus and tensile modulus which includes polycaprolactone polymer and an elastomeric polymer. Preferably at least one percent by weight of the polymeric material of the tray is elastomeric polymer. More preferably, at least 10 percent of the polymeric material of the tray is elastomeric polymer. Most preferably at least 20 percent of the polymeric material of the tray is elastomeric polymer. Preferred elastomeric polymer is amorphous or non-crystaline polymer, for example acrylonitrile butadiene styrene polymer (ABS polymer). Thus, preferred trays are formed of a polymer composition, having improved strength and stiffness in the cool state, which includes polycaprolactone, a glassy amorphous polymer, and an inorganic filler material. Preferably at least 50 to 75 percent by weight of the polymer composition is polycaprolactone, at least 1 to 20 percent is a glassy amorphous polymer, and 5 to 30 percent is an inorganic filler material. More preferably at least 50 to 70 percent of the polymer composition is polycaprolactone, at least 5 to 15 percent is composed of a glassy amorphous polymer, and at least 20 to 30 percent in an inorganic filler material. Most preferably about 50 percent of the polymer composition is polycaprolactone, about 20 percent of the composition is a glassy amorphous polymer and about 30 percent is an inorganic filler material. The preferred glassy amorphous polymer is a copolymer of styrene and acrylonitrile monomers and butadiene (ABS polymer) wherein the acrylonitrile content is between 24 and 30 mole percent, while the preferred inorganic filler material is a finely milled quartz.

In another embodiment of the invention, trays are formed of a polymeric material having improved draping characteristics in the warm state, (i.e. an ability to drape over and around an anatomical prominence like a tooth or gingival ridge) which includes polycaprolactone, an elastomeric polymer, and an inorganic filler material. Preferably at least 50 to 75 percent by weight of the polymer composition is polycaprolactone, at least 1 to 20 percent is an elastomeric polymer, and 5 to 30 percent is an inorganic filler material. More preferably at least 50 to 70 percent of the polymer composition is polycaprolactone, at least 5 to 15 percent is composed of an elastomeric polymer, and at least 20 to 30 percent in an inorganic filler material. Most preferably about 50 percent of the polymer composition is polycaprolactone, about 20 percent of the composition is an elastomeric polymer and about 30 percent is an inorganic filler material. Suitable elastomeric polymers include thermoplastic polyurethanes, polybutadiene, natural rubber, and certain predominately amorphous poly(alkyl vinyl ethers) particularly poly(ethyl vinyl ether) and poly(butyl vinyl ether). Suitable inorganic filler materials include, finely milled quartz and calcium carbonate.

Another embodiment of the invention provides an adjustable (heat-formable) tray having a wax bite block. The tray is made by injection molding pellets of about 34% inorganic filler, 7% styrene-butadiene polymer (a styrenic polymer) and 59% polycaprolactone (MW 37,000). Styrenic polymer is about 12% of the polymer composition of the tray. The styrenic polymer beneficially provides stiffness in the tray. The styrenic polymer beneficially increases the viscosity of the tray molding material during molding of the tray.

Preferably the adjustable (heat-formable) tray in the combination of the invention is from 0.5 to 60 percent by weight inorganic or organic filler particles. More preferably the adjustable (heat-formable) tray in the combination of the invention is from 1 to 40 percent by weight inorganic or organic filler particles.

Preferably the adjustable (heat-formable) tray in the combination of the invention includes thermoplastic polymer, such as styrene-butadiene polymer, having a softening point higher than 100° C. More preferably the adjustable (heat-formable) tray in the combination of the invention includes thermoplastic polymer having a softening point higher than 120° C.

Preferably the wax of the bite block has a higher melting point than the thermoplastic polymer of the tray. Preferably the wax of the bite block has a higher softening point than the thermoplastic polymer of the tray. Preferably the wax of the bite block has a melting point at least 5° C. higher than the thermoplastic polymer of the tray. Preferably the wax of the bite block has a softening point at least 5° C. higher than the softening point than the thermoplastic polymer of the tray.

The following examples are offered to aid in understanding the invention and are not to be construed as limiting its scope. Unless otherwise indicated, all parts and percentages are by weight.

EXAMPLE 1

10,000 grams of polycaprolactone powder and 10,000 grams of ABS polymer powder are mixed together and then warmed to 100° C. to form a liquid. The liquid is injection molded in a mold to form a U-shaped dental impression tray having a flat side with perforations opposite to a U-shaped side. A warm U-shaped wax bite registration member is adhered by pressing it onto the perforations of the flat side of the dental impression tray, for wax retention, and allowing it to cool.

EXAMPLE 2

A sheet of polycaprolactone is warmed to 80° C. and vacuum formed in a mold into a U-shaped dental impression tray having a flat side with perforations opposite to a U-shaped side. A warm U-shaped wax bite registration member is adhered by pressing it onto the perforations of the flat side of the dental impression tray, for wax retention, and allowing it to cool.

EXAMPLE 3

Upper and lower dental impression trays made as described in EXAMPLE 1 are each heated to a softened state at 71° C. The dimension of each dental impression tray is adjusted to fit the dental tissue in a patient's mouth. The heat adjustable material is cooled so that it solidifies. In turn dental impression material is placed in each custom fitting variable dimension bite registration dental impression tray. Then the patient's tissue is enveloped with the dental impression material, to form upper and lower dental tissue impressions of the dental tissue in the patient's mouth.

Then the upper and lower wax bite blocks (wax rims) are adjusted to record the patient's esthetic record and vertical dimension of occlusion. Thus, the wax bite blocks (bite registration members) are thereby each modified to a final position and marked by the dentist to record information including patient's smile line and mid line. Occlusal record material is then applied to the upper and lower wax bite blocks (upper and lower bite registration members) to hold them in a position representative of the patient's bite registration.

EXAMPLE 4

Upper and lower dental impression trays made as described in EXAMPLE 2 are each heated to a softened state at 71° C. The dimension of each dental impression tray is adjusted to fit a model of a patient's dental tissue. The heat adjustable material is cooled so that it solidifies. In turn dental impression material is placed in each custom fitting variable dimension bite registration dental impression tray. Then the patient's tissue is enveloped with the dental impression material, to form upper and lower dental tissue impressions of the dental tissue in the patient's mouth.

Then the upper and lower wax bite blocks (wax rims) are adjusted to record the patient's esthetic record and vertical dimension of occlusion. Thus, the wax bite blocks (bite registration members) are thereby each modified to a final position and marked by the dentist to record information including patients smile line and mid line. Occlusal record material is then applied to the upper and lower wax bite blocks (upper and lower bite registration members) to hold them in a position representative of the patient's bite registration.

The invention provides a heat formable dental impression tray having a wax bite block. In accordance with a preferred embodiment of the invention the heat adjustable material comprises a polycaprolactone. Preferably the softened heat adjustable material is in the form of an arch-shaped tray. Preferably the heat formable tray has a melting point lower than the melting point of the wax and above 38° C. Preferably the softening point of the heat formable tray is above 38° C. and below 90° C. In order of increasing preference the softening point of the wax is less than 95, 90, 85, or 80° C.

A preferred embodiment of the invention provides a method for making an impression of dental tissue, comprising the steps of: a) providing a custom fitting variable dimension bite registration dental impression tray, comprising a bite registration member, and a dental impression tray, b) placing said bite registration dental impression tray into a patient's mouth, c) removing the bite registration dental impression tray from said patient's mouth, d) heating the dental impression tray to softened state, the heat adjustable material being solid at 38° C. and having a softening point that comfortably can be withstood by oral tissues, e) adjusting the dimension of the dental impression tray, f) cooling the heat adjustable material so that it solidifies; and g) placing the adjusted bite registration dental impression tray into a patient's mouth and h) enveloping dental tissue in the patient's mouth with the dental impression material, whereby a dental tissue impression is obtained. Preferably the dental impression tray supports dental impression material.

A preferred embodiment of the invention provides a custom fit variable dimension bite registration dental impression tray formed by the process comprising the steps of: a) providing a variable dimension bite registration dental impression tray, comprising a bite registration member, and a dental impression tray, b) placing the bite registration dental impression tray into a patient's mouth, c) removing the bite registration dental impression tray from the patient's mouth, d) heating the dental impression tray to softened state, the heat adjustable material being solid at 38° C. and having a softening point that comfortably can be withstood by oral tissues, e) adjusting the dimensions of the dental impression tray, and f) cooling the heat adjustable material so that it solidifies; to form a custom fit variable dimension bite registration dental impression tray. Preferably the method further comprises g) placing the adjusted bite registration dental impression tray into a patient's mouth. Preferably the dental impression tray supports dental impression material. Preferably the method further comprises h) enveloping dental tissue in the patient's mouth with the dental impression material, and i) having the patient bite the bite registration member, whereby a dental tissue impression and bite registration of the patient's mouth are obtained.

A preferred embodiment of the invention provides a custom fitting variable dimension dental impression tray. The dental impression tray comprises heat adjustable material having a softening point above 38° C. and below 120° C. The heat adjustable material comprises from about 0.1 to about 99 percent by weight of polycaprolactone from about 0.1 to about 40 percent by weight of amorphus polymer. Preferably the polycaprolactone comprises 50 to 70 percent of the heat adjustable material. Preferably the tray is affixed to a bite registration member. Preferably the heat adjustable material further comprises at least 5 percent by weight of filler. Preferably the said bite registration member comprises wax adhered to said tray.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A custom fitting variable dimension bite registration dental impression tray, comprising:
   a bite registration member, and
   a dental impression tray,
   said bite registration member comprising wax,
   said dental impression tray comprising
   polycaprolactone having a softening point above 38° C. and below 120° C.

2. The tray of claim 1 wherein said tray comprises less than 50 percent by weight polycaprolactone and at least one percent by weight of elastomeric polymer.

3. The tray of claim 1 wherein said dental impression tray supports dental impression material.

4. The tray of claim 3 wherein said dental impression material has a final dental impression therein and said bite registration member has a bite registration and esthetic record.

5. The tray of claim 3 wherein said polycaprolactone is within the scope of the formula:

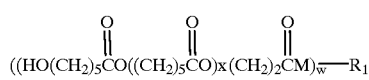

where $R_1$ is hydrogen, an aromatic moiety or an aliphatic moiety,
w is 1 if $R_1$ is hydrogen, otherwise w has an average value between 1 and 4, M is oxygen or —$NR_2$— where $R_2$ is hydrogen, an aromatic group or aliphatic group, and
w multiplied by x is equal to a number greater than about 35.

6. The tray of claim 1 wherein the softening point of said wax is less than 95° C.

7. A custom fitting variable dimension bite registration dental impression tray, comprising:
   a bite registration member, and
   a dental impression tray,
   said bite registration member comprising readily shaveable and inscribable material,
   said dental impression tray comprising a heat adjustable thermoplastic polymeric material having a softening point above 38° C. and below 120° C.

8. The tray of claim 7 wherein said heat adjustable material comprises polycaprolactone.

9. The tray of claim 7 wherein said bite registration member comprises wax.

10. The tray of claim 7 wherein said dental impression tray supports dental impression material.

11. The tray of claim 10 wherein said dental impression material has a final dental impression therein and said bite registration member has a bite registration and esthetic record.

12. The tray of claim 9 wherein the softening point of said wax is less than 95° C., and further comprising at least 1 percent by weight of thermoplastic polymer having a softening point higher than 100° C.

13. A method for making an impression of dental tissue, comprising the steps of:
   a) providing a custom fitting variable dimension bite registration dental impression tray, comprising a bite registration member, and a dental impression tray formed of a heat-softenable material, said dental impression tray supporting dental impression material,
   b) heating said dental impression tray to softened state, said heat adjustable material being solid at 38° C. and having a softening point that comfortably can be withstood by oral tissues,
   c) adjusting the dimensions of said dental impression tray,
   d) cooling the heat adjustable material so that it solidifies; and
   e) enveloping the tissue with said dental impression material, whereby a dental tissue impression is obtained.

14. The method of claim 13, wherein the heat adjustable material comprises a polycaprolactone.

15. The method of claim 13, wherein the heat adjustable material is in the form of a warm arch-shaped tray.

16. A dental impression tray comprising a heat formable impression tray connected to a wax bite block,
   said heat formable impression tray comprises thermoplastic polymer having a softening point,
   said wax has a softening point at least 5° C. higher than the softening point of said thermoplastic polymer.

17. The tray of claim 16 wherein said heat formable tray has a melting point lower than the melting point of said wax and above 38° C.

18. The heat formable tray of claim 16 wherein said heat formable tray has a melting point above 38° C., and said wax has a melting point less than 120° C.

19. A method for making an impression of dental tissue, comprising the steps of:
   a) providing a custom fitting variable dimension bite registration dental impression tray, comprising a bite registration member, and a dental impression tray formed of a heat-softenable material, b) placing said bite registration dental impression tray into a patient's mouth, c) removing said bite registration dental impression tray from said patient's mouth, d) heating said dental impression tray to softened state, said heat adjustable material being solid at 38° C. and having a softening point that comfortably can be withstood by oral tissues, e) adjusting the dimensions of said dental impression tray, f) cooling the heat adjustable material so that it solidifies; and g) placing said adjusted bite registration dental impression tray into a patient's mouth.

h) enveloping dental tissue in the patient's mouth with said dental impression material, whereby a dental tissue impression is obtained.

20. The method of claim 19 further comprising biting said bite registration member while said bite registration member is in the patient's mouth.

21. A custom fit variable dimension bite registration dental impression tray formed by the process comprising the steps of:

a) providing a variable dimension bite registration dental impression tray, comprising a bite registration member, and a dental impression tray formed of a beat-softenable material, b) placing said bite registration dental impression tray into a patient's mouth, c) removing said bite registration dental impression tray from said patient's mouth, d) heating said dental impression tray to softened state, said heat adjustable material being solid at 38° C. and having a softening point that comfortably can be withstood by oral tissues, e) adjusting the dimensions of said dental impression tray, and f) cooling the heat adjustable material so that it solidifies; to form a custom fit variable dimension bite registration dental impression tray.

22. The product of claim 21 further comprising g) placing said adjusted bite registration dental impression tray into a patient's mouth.

23. The product of claim 21 wherein said dental impression tray supports dental impression material.

24. The product of claim 21 further comprising h) enveloping dental tissue in the patient's mouth with said dental impression material, and i) having said patient bite said bite registration member, whereby a dental tissue impression and bite registration of the patient's mouth are obtained.

25. A custom fitting variable dimension dental impression tray, comprising:

a dental impression tray, and a bite registration member, said dental impression tray comprising heat adjustable material having a softening point above 38° C. and below 120° C., said heat adjustable material comprising from about 0.1 to about 99 percent by weight of polycaprolactone from about 0.1 to about 40 percent by weight of amorphous polymer.

26. The tray of claim 25 wherein said polycaprolactone comprises 50 to 70 percent of said heat adjustable material.

27. The tray of claim 25 wherein said heat adjustable material further comprises thermoplastic polymer and at least 5 percent by weight of inorganic filler, said thermoplastic polymer has a softening point, and said bite registration member comprises wax, said wax has a softening point at least 5° C. higher than the softening point of said thermoplastic polymer.

28. The tray of claim 25 wherein said amorphous polymer is an acrylonitrile butadiene styrene polymer.

29. The tray of claim 25 wherein said amorphous polymer is an elastomeric polymer.

* * * * *